(12) United States Patent
Gutman et al.

(10) Patent No.: US 9,233,898 B2
(45) Date of Patent: Jan. 12, 2016

(54) PROCESS FOR THE PREPARATION OF 2-PHENYL-1,3-PROPANEDIOL

(75) Inventors: Daniella Gutman, Rishon Lezion (IL); Wael Baidossi, Kafr-Qara (IL); Sorin Bercovici, Kiryat-Ono (IL); Simon Cherniak, Haifa (IL)

(73) Assignee: TARO PHARMACEUTICAL INDUSTRIES LTD., Haifa Bay (IL)

( * ) Notice: Subject to any disclaimer, the term of this patent is extended or adjusted under 35 U.S.C. 154(b) by 223 days.

(21) Appl. No.: 13/821,475

(22) PCT Filed: Sep. 5, 2011

(86) PCT No.: PCT/IL2011/000705
§ 371 (c)(1),
(2), (4) Date: May 20, 2013

(87) PCT Pub. No.: WO2012/032508
PCT Pub. Date: Mar. 15, 2012

(65) Prior Publication Data
US 2013/0231496 A1 Sep. 5, 2013

Related U.S. Application Data

(60) Provisional application No. 61/380,334, filed on Sep. 7, 2010.

(51) Int. Cl.
C07C 29/147 (2006.01)
C07C 29/149 (2006.01)
C07C 29/86 (2006.01)
C07C 271/12 (2006.01)
C07C 269/00 (2006.01)

(52) U.S. Cl.
CPC ............. *C07C 29/147* (2013.01); *C07C 29/149* (2013.01); *C07C 29/86* (2013.01); *C07C 269/00* (2013.01); *C07C 271/12* (2013.01)

(58) Field of Classification Search
CPC .. C07C 269/00; C07C 271/12; C07C 29/147; C07C 29/86
USPC .......................................... 560/164; 568/811
See application file for complete search history.

(56) References Cited

U.S. PATENT DOCUMENTS

| 2,884,444 | A | 4/1959 | Berger et al. |
| 4,868,327 | A | 9/1989 | Stiefel |
| 4,978,680 | A | 12/1990 | Sofia |
| 4,982,016 | A | 1/1991 | Choi |
| 5,082,861 | A | 1/1992 | Sofia |
| 5,091,595 | A | 2/1992 | Choi |
| 5,500,484 | A | 3/1996 | Iwasaki et al. |
| 2010/0160290 | A1 | 6/2010 | Kobayashi et al. |

FOREIGN PATENT DOCUMENTS

| WO | WO-94/06737 A1 | 3/1994 |
| WO | WO-94/27491 A2 | 12/1994 |

OTHER PUBLICATIONS

International Search Report issued in PCT/IL2011/000705 dated Jan. 17, 2012.
Written Opinion issued in PCT/IL2011/000705 dated Jan. 17, 2012.
Loev et al., "t-Butyl Carbamate," Organic Synthesis Collective. vol. 5 p. 162 (1973).

*Primary Examiner* — Paul A Zucker
*Assistant Examiner* — Mark Luderer

(57) ABSTRACT

The present invention is related to a novel synthetic procedure that provides a simple, safe and commercially valuable method for the preparation of 2-phenyl-1,3-propanediol. The process for the preparation of 2-phenyl-1,3-propanediol involves reducing diethyl phenylmalonate with sodium borohydride ($NaBH_4$) in the presence of an alkali metal dihydrogen phosphate buffer or the hydrate thereof.

20 Claims, No Drawings

PROCESS FOR THE PREPARATION OF 2-PHENYL-1,3-PROPANEDIOL

CROSS REFERENCE TO RELATED APPLICATIONS

This Application is a U.S. National Stage of International Application No. PCT/IL2011/000705, filed Sep. 5, 2011, which claims benefit under 35 U.S.C.§119(e) of U.S. Provisional Application No. 61/380,334, filed Sep. 7, 2010, each of which is incorporated by reference in its entirety.

FIELD OF THE INVENTION

The present invention relates to the preparation process of 2-phenyl-1,3-propanediol which may be used as a starting material for the synthesis of Felbamate (2-phenyl-1,3-propanediol dicarbamate).

BACKGROUND OF THE INVENTION

Felbamate, also known as 2-phenyl-1,3-propanediol dicarbamate, having the structure of Formula (I),

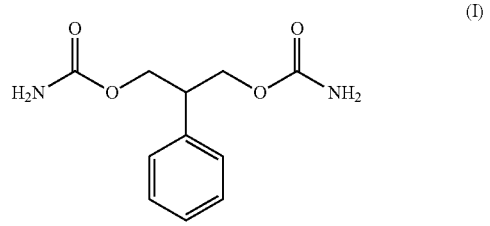 [SMILES: NC(=O)OCC(COC(N)=O)c1ccccc1]

Felbamate is a well known antiepileptic drug described in U.S. Pat. Nos. 4,978,680 and 5,082,861.

Several processes for the synthesis of Felbamate have been described, including the methods disclosed in U.S. Pat. Nos. 2,884,444, 4,868,327, 4,982,016, 5,091,595 and 5,500,484, as well as WO 94/06737 and WO 94/27491, all of which are incorporated by reference.

The compound 2-phenyl-1,3-propanediol of Formula (II)

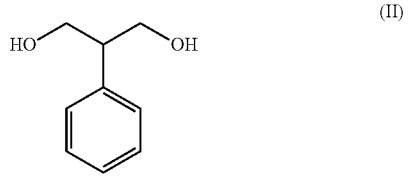 [SMILES: OCC(CO)c1ccccc1]

is used as an intermediate for Felbamate synthesis. U.S. Pat. Nos. 2,884,444, 4,982,016 and 5,091,595 teach the synthesis of 2-phenyl-1,3-propanediol by reduction of the corresponding 2-substituted malonic ester, diethyl phenylmalonate, with metal hydride complexes. However, the above methods require costly and extremely flammable agents for reducing diethyl phenylmalonate to 2-phenyl-1,3-propanediol such as borane dimethyl sulfide, lithium aluminum hydride and diisobutyl aluminum hydride. The high cost and hazardous nature of these reducing agents render such processes unsatisfactory for commercial use. In addition, the yield of the 2-phenyl-1,3-propanediol preparation using the above methods is between about 30% to about 50% and the impurity levels were found to be relatively high.

Zhao et al. and Goto M. et al. (Chinese Journal of New Drugs, 2005, Vol 14, No. 12 and Research Reports of Toyama National College of Technology, 2001, Vol 35, respectively) disclose 2-phenyl-1,3-propanediol preparation by the reduction of Diethyl Phenylmalonate with the nonflammable reducing agent Sodium Borohydride in the presence of Hydrochloric acid. However, the above method suffers from the drawback of high impurity levels and low yields of the product.

In view of the above it would be desirable to provide faster, facile, safer and more efficient process for the preparation of 2-phenyl-1,3-propanediol.

SUMMARY OF THE INVENTION

The present invention relates to a novel synthetic process that provides simple, safe and commercially valuable method for the preparation of 2-phenyl-1,3-propanediol.

The process for the preparation of 2-phenyl-1,3-propanediol of formula (II) involves reducing Diethyl Phenylmalonate of Formula (III) with sodium borohydride ($NaBH_4$) in the presence of an alkali metal dihydrogen phosphate or the hydrate thereof.

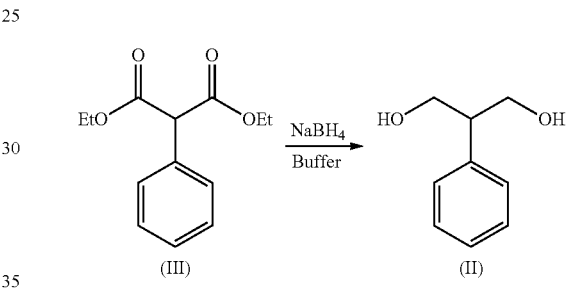

It was surprisingly found that the addition of the alkali metal dihydrogen phosphate buffer to the reaction mixture maintains a controlled pH in the range of about 5.0 to about 6.0 which increases the yield of the reaction and reduces the level of impurities.

Specifically, the addition of an alkali metal dihydrogen phosphate or the hydrate thereof maintains a controlled pH range of between about 5.0 to about 6.0 during the reaction, and reduces the formation of undesirable impurities, especially the formation of phenyl ethanol. As a result of the controlled pH, high yield and purity of 2-phenyl-1,3-propanediol are obtained. Preferred alkali metal dihydrogen phosphate buffers according to the present invention are sodium dihydrogen phosphate or potassium dihydrogen phosphate or the hydrates thereof.

According to one embodiment, the reaction between Diethyl Phenylmalonate of Formula (III) with sodium borohydride is performed in the presence of a buffer which maintains the reaction pH within the range of between about 5.0 to about 6.0. Under these pH conditions, the formation of undesirable impurities such as phenyl ethanol is greatly prevented.

In another embodiment, the present invention provides a process for reducing the amount of phenyl ethanol formed during the reaction between diethyl phenylmalonate and sodium borohydride by maintaining the reaction pH in the range of between about 5.0 to about 6.0. The pH range is preferably maintained by adding an alkali metal dihydrogen phosphate buffer to the reaction mixture in an amount sufficient to maintain the desired pH range. In a preferred embodiment, the alkali metal dihydrogen phosphate buffer added to the reaction mixture reduces the amount of 2-phenyl ethanol produced during the reaction to a level of not more than about 10%, more preferably to a level of not more than about 5%.

The 2-phenyl-1,3-propanediol preparation process of the invention comprises further purification steps after which the percentage of total impurities is not more than about 1%. The pH range obtained by the process of the present invention allows the synthesis of 2-phenyl-1,3-propanediol with a yield of between about 60% to about 70%, wherein the yield represents the percent weight of the obtained 2-phenyl-1,3-propanediol versus the expected theoretical weight.

In a preferred embodiment, the 2-phenyl-1,3-propanediol obtained by the process of the present invention is used as an intermediate for the synthesis of 2-phenyl-1,3-propanediol dicarbamate (Felbamate). The Felbamate obtained using the process of the present invention preferably comprises not more than about 0.05% of a single unknown or known impurity and more preferably not more than about 0.05% of total impurities.

In another embodiment, the present invention provides a process for preparing 2-phenyl-1,3-propanediol comprising the steps of:
(a) reacting diethyl phenylmalonate with sodium borohydride in the presence of an alkali metal dihydrogen phosphate or the hydrate thereof to yield 2-phenyl-1,3-propanediol;
(b) quenching the reaction of step (a);
(c) basifying the reaction mixture of step (b) and extracting the 2-phenyl-1,3-propanediol into an organic solvent to form an organic layer; and
(d) isolating the 2-phenyl-1,3-propanediol from the organic layer of step (c).

The process for preparing 2-phenyl-1,3-propanediol of the present invention provides higher yields and purity as compared to known processes. The process is also less hazardous and more cost-effective by utilizing conventional equipment for implementation on a large tonnage scale. The conversion of diethyl phenylmalonate to 2-phenyl-1,3-propanediol can be accomplished at high process throughput in a continuous process sequence suitable for the automated production of both 2-phenyl-1,3-propanediol and Felbamate. Such high process throughput or automated production can significantly reduce manufacturing costs.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

When utilizing herein the terms listed below, unless indicated otherwise, are defined as follows:

Felbamate as defined herein is the Active Pharmaceutical Ingredient (API) for treating epileptic seizures, also known as 2-phenyl-1,3-propanediol dicarbamate.

The term "buffer" as used herein, represents any reagent that can maintain the pH of the reaction between diethyl phenylmalonate and sodium borohydride within the range of between about 5.0 to about 6.0.

The term "yield of 2-phenyl-1,3-propanediol" as used herein is defined as the percent weight of the obtained 2-phenyl-1,3-propanediol versus the expected theoretical weight.

The reaction between diethyl phenylmalonate and sodium borohydride normally leads to a pH value of above 6.0 which allows the undesired hydrolysis of diethyl phenylmalonate and the spontaneous de-carboxylation leading to the formation of the main impurity, 2-phenyl ethanol. It has surprisingly been found that maintaining a pH range of between about 5.0 to about 6.0 during the reaction by the addition of a buffer, significantly diminishes the above side reaction and the formation of 2-phenyl ethanol.

In one embodiment, the preparation of 2-phenyl-1,3-propanediol involves mixing diethyl phenylmalonate with sodium dihydrogen phosphate in a polar solvent followed by the addition of sodium borohydride in diluted NaOH to the mixture to allow the reaction of diethyl phenylmalonate with sodium borohydride. In another embodiment, diethyl phenylmalonate is mixed with sodium dihydrogen phosphate monohydrate in a polar solvent followed by the addition of sodium borohydride. In yet another embodiment, the buffer used in the reaction is potassium dihydrogen phosphate or its hydrate.

The molar ratio between sodium dihydrogen phosphate or its hydrate to sodium borohydride is preferably between about 1:2 to 2:1, more preferably the molar ratio between sodium dihydrogen phosphate or its hydrate to sodium Borohydride is 1:1.

The polar solvent suitable for the reaction may be for example dioxane, tetrahydrofuran (THF), dimethoxyethane (Glyme), bis(2-methoxyethyl)ether (Diglyme) isopropyl alcohol or ethanol, or any combination thereof Preferred polar solvent to be used in the reaction is ethanol.

The reaction temperature employed in the present invention is in the range from about 0° C. to about 50° C., preferably from about 0° C. to about 15° C., more preferably from about 0° C. to about 10° C., most preferably from about 5° C. to about 7° C. In another embodiment, the temperature of the reaction is in the range from about 10° C. to about 15° C.

The duration of the reaction between diethyl phenylmalonate and sodium borohydride is between about 30 minutes to about 3 hours, more preferably between about 1 hour to about 2 hours. The reaction is then quenched with a strong inorganic acid. Preferred strong inorganic acid is $H_2SO_4$ in a concentration of between about 3% to about 10% or a solution of HCl in a concentration of between about 5% to about 15%, more preferred is a solution of HCl in a concentration of about 10%. In another embodiment the reaction is quenched by the addition of water followed by heating to a temperature of between about 40° C. to about 60° C., preferably between about 50° C. to about 60° C.

Following the quenching of the reaction, sodium hydroxide solution is added in order to basify the solution. Ethyl acetate is then used for extraction of the 2-phenyl-1,3-propanediol product into the organic layer.

The isolation of 2-phenyl-1,3-propanediol is completed by washing the organic layer with a polar solvent, preferably with distilled water followed by evaporation and crystallization with an organic solvent, for example with a halogenated aromatic solvent or an alkylated aromatic solvent. Preferred organic solvent for crystallization is chlorobenzene, toluene or xylene. Most preferred organic solvent is toluene.

The yield of 2-phenyl-1,3-propanediol obtained by the process of the present invention is preferably between about 60% to about 70% with at least 96% purity, more preferably at least 98% purity, and most preferably at least 99% purity.

The 2-phenyl-1,3-propanediol produced by the process of the present invention may be used as an intermediate for Felbamate synthesis as disclosed for example in WO94/06737 and in Organic Synthesis Collective. vol. 5 p. 162 (1973). Specifically, 2-phenyl-1,3-propanediol may be mixed with sodium cyanate and trichloroacetic acid (TCAA) in the presence of a suitable solvent as known in the art to yield Felbamate.

EXAMPLES

Example I

Synthesis of 2-Phenyl-1,3-Propanediol

Sodium dihydrogen phosphate (58.3 g) was added to a solution of 50 g of diethyl phenylmalonate in 350 ml of ethanol. The mixture was cooled to 5-7° C. and a solution of 16.7 g of sodium borohydride in 38 ml of 0.2% NaOH was gradually added. The mixture was stirred for additional 2 hours and the Ethanol was distilled out. The reaction was quenched by adding 132 ml of water followed by heating to 50° C.-60° C. for 2 hours. The solution was then basified with 50% NaOH and extracted with ethyl acetate. The organic layer was washed with water and evaporated to dryness. The precipitate was crystallized from toluene. 20 g of 2-phenyl-1,3-propanediol was obtained with a yield of 63%.

Example II

Synthesis of 2-Phenyl-1,3-Propanediol

A mixture of 20 g of diethyl phenylmalonate, 6.6 g of sodium dihydrogen phosphate monohydrate and 140 ml of absolute ethanol was cooled to 15° C. after which 7.1 g of solid sodium borohydride was added. The reaction was completed by quenching the excess of sodium borohydride with 10% HCl solution and distilling the residual ethanol. 8 ml of NaOH 50% were added in order to obtain a pH of between about 8.0 to about 9.0. The obtained 2-phenyl-1,3-propanediol was then extracted into 400 ml of ethyl acetate. The organic layer was washed with 40 ml of water and filtered through alumina. The precipitate was crystallized from toluene following solvent removal, to obtain 8.9 g of 2-phenyl-1,3-propanediol with a yield of 69%.

Example III

Synthesis of Felbamate

A mixture of 120 kg of 2-phenyl-1,3-propanediol, 132 kg of sodium cyanate and 600 L of toluene was charged into a reactor and heated to 45° C. followed by the addition of 400 kg of trichloroacetic acid. The reaction mixture was stirred for 1 hr at 45° C. and then was brought to reflux for 4 hr. The reaction mixture was cooled to room temperature and then to 10° C. for 1 hr with stirring. Solids particles were filtered out and the remaining solution cake was washed with water in order to get a pH of at least 8. The obtained wet crude Felbamate was purified by crystallization form Methanol and was dried in a vacuum oven to yield Felbamate with at least 99% purity.

Example IV

The effect of buffer on the impurities formed during the synthesis of 2-Phenyl-1,3-Propanediol The use of sodium borohydride in the preparation of 2-Phenyl 1,3 Propandiol leads to the development of basic pH conditions during the reaction. These pH conditions promote the formation of 2-phenyl ethanol which leads to low purity and low yield of the 2-phenyl-1,3-propanediol product.

The formation of 2-phenyl ethanol during the reaction between diethyl phenylmalonate and sodium borohydride was determined in the presence or absence of sodium dihydrogen phosphate as a buffer. As demonstrated in Table 1, the addition of the buffer to the reaction significantly reduced the formation of 2-phenyl ethanol and led to the formation of highly purified 2-phenyl-1,3-propanediol. The purity of 2-phenyl-1,3-propanediol obtained in the presence of the buffer is significantly higher than the purity obtained using the standard reaction (91.6% purity versus 60% purity, respectively). Furthermore, the percentage of the 2-phenyl ethanol impurity which was produced in the presence of buffer was greatly reduced (4.7% of 2-phenyl ethanol when buffer was added to the reaction versus 10% of 2-phenyl ethanol in the absence of buffer). The percentage of other non-identified impurities (Impurity A and Impurity B) was also greatly reduced when the buffer was added to the reaction (for example, 0.14% of impurity A when the buffer was added to the reaction versus 1.8% of impurity A in the absence of buffer). The 2-phenyl-1,3-propanediol preparation process of the invention comprises further purification steps after which the percentage of total impurities is not more than about 1%.

TABLE 1

The effect of buffer addition on impurity formation during the reaction

|  | 2-Phenyl-1,3-Propanediol purity (%) | 2-phenyl ethanol (%) | Impurity A (%) | Impurity B (%) |
|---|---|---|---|---|
| Reaction without sodium dihydrogen phosphate | 60 | 10 | 1.8 | 12.5 |
| Reaction with sodium dihydrogen phosphate | 91.6 | 4.7 | 0.14 | 3.6 |

What is claimed is:

1. A process for preparing 2-phenyl-1,3-propanediol comprising the steps of:
   (a) reacting diethyl phenylmalonate with sodium borohydride in the presence of an alkali metal dihydrogen phosphate or the hydrate thereof to yield 2-phenyl-1,3-propanediol;
   (b) quenching the reaction of step (a);
   (c) basifying the reaction mixture of step (b) and extracting the 2-phenyl-1,3-propanediol into an organic solvent to form an organic layer; and
   (d) isolating the 2-phenyl-1,3-propanediol from the organic layer of step (c).

2. The process of claim 1, wherein the alkali metal dihydrogen phosphate of step (a) is sodium dihydrogen phosphate or the hydrate thereof, or potassium dihydrogen phosphate or the hydrate thereof.

3. The process of claim 2, wherein the alkali metal dihydrogen phosphate of step (a) is sodium dihydrogen phosphate monohydrate or potassium dihydrogen phosphate monohydrate.

4. The process of claim 1, wherein the alkali metal dihydrogen phosphate maintains the pH of the reaction of step (a) within a range of between about 5.0 to about 6.0.

5. The process of claim 1, wherein the reaction of step (a) is performed in the presence of a polar solvent.

6. The process of claim 5, wherein the polar solvent is selected from the group consisting of dioxane, tetrahydrofuran (THF), dimethoxyethane (Glyme), bis(2-methoxyethyl) ether (Diglyme), isopropyl alcohol and ethanol, or any combination thereof.

7. The process of claim 6, wherein the polar solvent is ethanol.

8. The process of claim 1, wherein the molar ratio between the alkali metal dihydrogen phosphate or its hydrate and the sodium borohydride is between about 1:2 to about 2:1.

9. The process of claim 1, wherein the reaction of step (a) is performed at a temperature of between about 0° C. to about 50° C.

10. The process of claim 9, wherein the reaction of step (a) is performed at a temperature of between about 0° C. to about 15° C.

11. The process of claim 1, wherein the duration of the reaction of step (a) is between about 30 minutes to about 3 hours.

12. The process of claim 11, wherein the duration of the reaction of step (a) is between about 1 hour to about 2 hours.

13. The process of claim 1, wherein step (b) comprises quenching the reaction of step (a) with a strong inorganic acid or water.

14. The process of claim 13, wherein the strong inorganic acid is HCl or $H_2SO_4$.

15. The process of claim 1, wherein the isolation of 2-phenyl-1,3-propanediol of step (d) comprises crystallization with an organic solvent.

16. The process of claim 15, wherein the organic solvent is a halogenated aromatic solvent or an alkylated aromatic solvent.

17. The process of claim 16, wherein the halogenated aromatic solvent is chlorobenzene.

18. The process of claim 16, wherein the alkylated aromatic solvent is xylene or toluene.

19. A process for the preparation of 2-phenyl-1,3-propanediol dicarbamate (Felbamate) comprising preparing 2-phenyl-1,3-propanediol according to the method of claim 1 as an intermediate material; and converting the 2-phenyl-1,3-propanediol to Felbamate.

20. The process of claim 1, wherein the organic solvent of step (c) is ethyl acetate.

* * * * *